United States Patent [19]
Hendricks et al.

[11] Patent Number: 5,137,815
[45] Date of Patent: Aug. 11, 1992

[54] PRODUCTION OF MICROORGANISMS HAVING ICE NUCLEATING ACTIVITY

[75] Inventors: Donna M. Hendricks; Patrick J. Ward; Shirley A. Orrego, all of Rochester, N.Y.

[73] Assignee: Genencor International, So. San Franscisco, Calif.

[21] Appl. No.: 910,600

[22] Filed: Sep. 23, 1986

[51] Int. Cl.$^5$ ............ C12N 15/00; C12N 1/20; C12P 1/04
[52] U.S. Cl. ............ 435/172.1; 435/252.1; 435/253.3; 435/170
[58] Field of Search ............ 435/170, 172.1, 822, 435/874, 252.1, 253.3

[56] References Cited
U.S. PATENT DOCUMENTS 4,200,228 4/1980 Woerpel ............ 239/25

OTHER PUBLICATIONS

Lindow et al., Phytopathology, 68 (3) 1978, pp. 523–528.
Bergey's Manual of Sytematic Bacteriology, vol. 1, 1984, pp. 141–148.
Maki & Willoughby, Bacteria as Biogenic Sources of Freezing Nuclei, J. Applied Meteorology 17, 1049–1053.
Kozloff Schofield and Lute, Ice Nucleating Activity of *Pseudomonas Syringae* and *Erwinia herbicola*, J. Bacter 153, pp. 222–231 (1983).

*Primary Examiner*—Irene Marx
*Attorney, Agent, or Firm*—James G. Passe

[57] ABSTRACT

A method for the fermentation of microorganisms having a high level of ice nucleating activity is disclosed. The method includes the step of adding acid to the fermentation medium when the pH approaches about 6.7 and adding base when the pH approaches about 5.5.

9 Claims, No Drawings

PRODUCTION OF MICROORGANISMS HAVING ICE NUCLEATING ACTIVITY

FIELD OF THE INVENTION

The present invention relates to a method for the fermentation of microorganisms that have ice nucleating activity.

DESCRIPTION RELATIVE TO THE PRIOR ART

In U.S. Pat. No. 4,200,228 there is disclosed a method for the making of snow whereby microorganisms are included in droplets that are sprayed into the air. The microorganisms that are used are of the type which are known to promote ice nucleation. As a result, snow can be made at temperatures that are much higher than are ordinarily possible. A typical microorganism that is useful in this process is a Pseudomonad and particularly *Pseudomonas syringae*.

It is apparent that if this process is to be used on any scale, large amounts of microorganisms are needed. Further, it is desirable that the microorganism be obtained in a dry form so as to facilitate the storage handling and transport of the material.

The growth conditions for microorganisms that have ice nucleating activity are known in the art. For example, in Maki and Willoughby, Bacteria as Biogenic Sources of Freezing Nuclei, J. Applied Meteorology 17 1049-1053 it is disclosed that the microorganisms such as *Pseudomonas syringae* are grown in Koser citrate broth at a temperature below 20° C., i.e. 5° C. This medium is well known and has a pH of about 6.7. No control of the pH is disclosed in this reference. It is also stated that if the cultures are grown at a temperature above 20° C., very few freezing nuclei are produced.

As far as the recovery process is concerned, this reference discloses that concentrated cultures that had been treated with formalin were freeze dried. No details are given.

In another reference, the microorganisms are grown on a tryptone-yeast extract-glycerol medium which would have a pH of about 7.0. (Kozloff, Schofield and Lute, Ice Nucleating Activity of Pseudomonas syringae and Erwinia herbicola, J. Bacter. 153 pages 222-231 (1983)). In this reference, the microorganisms are not recovered in dry form and the suspensions are tested directly for activity. It is noted that the ice nucleating activity is not stable in the suspension and decreases overnight.

If the known procedures are used for the production of large volumes of the microorganisms, less than the desired ice nucleating activity is obtained. Not only is the ice nucleating activity of the initial suspension less than desired, but much of the activity is lost during the freeze drying of large volumes of the material. The end result is a process that is not capable of producing commercial quantities of microorganism at reasonable cost. It is to the solution of this problem that the present invention is directed.

SUMMARY OF THE INVENTION

The present invention is an improved method for the fermentation of a microorganism which has ice nucleating activity comprising the steps of fermenting said microorganism in a fermentation medium and recovering said microorganism. The improvement comprises adding acid to said fermentation when the pH approaches about 6.7 and adding base to said medium when the pH approaches about 5.5.

DETAILED DESCRIPTION OF THE INVENTION

In conventional fermentation processes, the pH of the fermentation medium is either allowed to vary or is maintained at a fixed pH value as closely as possible. In the references cited above, since there is no discussion of pH control, it is assumed that the pH was allowed to vary. These fermentations are also conventional in that the fermentation starts out at neutrality, that is, a pH of close to 7.0. In such a conventional fermentation, the pH will vary over a wide range. Typically, the pH will initially drop as acids are produced by the fermenting organisms. Then, as the fermentation continues, the pH will rise. Typically the pH can get as low as 5.0 and as high as 8.0 if there is no control.

In the case of ice nucleating microorganisms, the ice nucleating activity (INA) of the microorganisms is substantially improved if the pH of the fermentation medium is allowed to vary but only between about pH 6.7 and 5.5 and preferably only between 6.6 and 5.6. If the pH is maintained at the midpoint of this range, pH 6.1, or at another pH such as 6.8, the INA is inferior. Similarly, if the pH of the fermentation is allowed to vary over a wide range, the INA is also inferior. The reason for this phenomenon is not understood.

The process of controlling the pH in the manner required by the present invention is within the skill of those in the art. Acid can be added as the pH approaches 6.7 at a rate sufficient to prevent the pH from substantially exceeding 6.7. As a typical example, for a 1500L fermentor, beginning to add acid at the rate of about 1 mL per liter of medium per minute when the pH reaches 6.7, for example, is sufficient. Base is added in an analogous manner. The pH control can be manual or automatic as is well known in this art.

Bases and acids which are added to control the pH are conventional. For convenience, sodium hydroxide and sulfuric acid can be used.

While improvements in the INA are seen at any fermentation temperature, we have found that the temperature is also important for optimum yield of INA. We have found that the optimum temperature is between 19° C. and 23° C. and is preferably 21° C. This was surprising since, as noted above, Maki and Willoughby used 5° C. and stated that cultures grown at 20° C. or higher produce very few freezing nuclei.

The present invention also provides an improvement with any fermentation medium but we have found a specific medium that provides still further improvements. The medium preferably contains, as the carbon source, glycerol or an alcohol sugar such as mannitol or sorbitol. The nitrogen source is preferably a complex source such as yeast extract. The presently preferred medium contains mannitol as the carbon source, yeast extract and magnesium sulfate. We have also found that, for optimum results, the initial concentration of these components is higher than would be expected. The currently preferred medium is given below in Table I.

TABLE I

| Component | Initial Concentration |
|---|---|
| mannitol | about 80 g/l |
| yeast extract | about 20 g/l |
| magnesium sulfate | about 1 g/l |

Any microorganism that has ice nucleation activity can be produced by the present invention. Suitable microorganisms include Pseudomonads such as *P. syringae* and *P. fluorscens, P. coronafaciens* and *P. pisi*. Other microorganisms that are useful in the present invention include *Erwina herbicola*. The presently preferred microorganism is *P. syringae* ATCC No. 53543 deposited on Sep. 23, 1986 in accordance with the Budapest Treaty with the American Type Culture Collection in Rockville, Md., USA.

The microorganism that is produced in the described fermentation can be dried in a number of ways. Spray drying and freeze drying are typical examples. Any drying process will reduce the INA to a certain extent. One preferred method that preserves a large amount of the INA that is produced in the fermentor is the process that is described in commonly assigned U.S. Pat. No. 4,706,463 issued Nov. 17, 1987 entitled "Recovery of Microorganisms Having Ice Nucleating Activity" of Lindsey. In this process, the medium is cooled, concentrated, run into a cryogenic liquid to form pellets and then the pellets are freeze dried at relatively low temperature.

In the examples presented below, the INA is calculated using conventional techniques. The INA is determined by placing a plurality of microorganism containing water droplets (10 $\mu$l) on paraffin coated aluminum foil. The foil is maintained at $-5°$ C. by placing it on a constant temperature bath. Details regarding this procedure are found in the literature, for example, Vali, Quantitative Evaluation of Experimental Results on the Heterogenous Freezing of Sypercooled Liquids, J. Atoms Sci., 28, 402–409 (1971). The INA reported in the examples is the number of ice nucleating sites per dry gram of microorganism. For the present purposes, the INA is measured using a sample directly from the fermentor without drying. It will therefore be referred to as "Fermentor INA". The units are nuclei per dry gram of microorganism.

The following examples are submitted for a further understanding of the invention.

EXAMPLE 1

*Pseudomonas syringae* ATCC 53543 was streaked on an agar plate containing a nutrient medium containing mannitol, yeast extract and magnesium sulfate. After 36 hours at 26° C., one half of the plate was used to innoculate a 500 ml flask also containing a similar medium.

After 14 hours at 26° C. this liquid seed was used to innoculate 8 liters of a fermentation medium to an optical density of about 0.75 to 1.0 optical density units measured at 600 nm. The medium was as described in Table I above except that it also contained 0.1 g/l of the antifoaming agent Struktol ® available from Struktol Corp, USA.

The fermentation temperature was controlled at 21° C. During the fermentation, the pH was controlled with 4N hydrochloric acid and 2N sodium hydroxide. The acid was added when the pH approached 6.6 and the base was added when the pH approached 5.6. The dissolved oxygen was maintained at greater than 30% saturation. The antifoaming agent was added as needed to control foaming.

After 36 hours, the cell mass reached 18 g dry cells/liter. The Fermentor INA was $5.0 \times 10^{11}$.

EXAMPLE 2

This is a comparative example.

Example 1 was repeated except that the pH was not controlled during the fermentation. The Fermentor INA was $1.66 \times 10^{11}$.

EXAMPLE 3

Example 1 was repeated except that the concentration of the components in the fermentation medium were decreased by one half. The Fermentor INA for this fermentation was $2.30 \times 10^{11}$.

EXAMPLE 4

This is a comparative example.

Example 3 was repeated except that the pH was controlled as in Example 1 when the pH approached 7.0 and 6.7. The Fermentor INA was $1.40 \times 10^{11}$.

TABLE II

Example Summary

| Example | pH control | Medium conc. | Fermentor INA $\times 10^{-11}$ |
|---|---|---|---|
| 1 | 6.6–5.6 | x | 5.0 |
| 2 (C) | none | x | 1.66 |
| 3 | 6.6–5.6 | 1/2x | 2.3 |
| 4 (C) | 7.0–6.7 | 1/2x | 1.40 |

The invention has been described in detail with particular reference to preferred embodiments thereof, but it will be understood that variations and modifications can be effected within the spirit and scope of the invention.

What is claimed is:

1. In a method for the production of a microorganism which has ice nucleating activity comprising the steps of culturing said microorganism in a fermentation medium and recovering said microorganism, the improvement comprises controlling the pH by adding acid to said fermentation medium when the pH approaches about 6.7 and adding base to said medium when the pH approaches about 5.5.

2. The method according to claim 1 wherein said pH is controlled between 6.6 and 5.6.

3. The method according to claim 1 wherein said microorganism is a Pseudomonad.

4. The method according to claim 3 wherein said microorganism is *P. syringae*.

5. The method according to claim 1 wherein said fermentation medium comprises glycerol or a sugar alcohol and yeast extract.

6. The method according to claim 5 wherein said fermentation medium comprises mannitol.

7. The method according to claim 5 wherein said fermentation medium comprises mannitol at a concentration of about 80 g/l and yeast extract at a concentration of about 20 g/l.

8. The method according to claim 1 wherein said fermentation is carried out at a temperature between 19° C. and 23° C.

9. The method according to claim 8 wherein said temperature is 21° C.

* * * * *